(12) United States Patent
Fujisaki et al.

(10) Patent No.: US 7,135,552 B2
(45) Date of Patent: Nov. 14, 2006

(54) MITE GALECTIN

(75) Inventors: Kozo Fujisaki, c/o Obihiro University of Agriculture and Veterinary Medicine National Research Center for Potozoan Diseases, 13 Nishinisen, Inada-cho, Obihiro-shi, Hokkaido 080-8555 (JP); Hideyuki Nagasawa, Hokkaido (JP); Ikuo Igarashi, Hokkaido (JP); Hiroshi Suzuki, Hokkaido (JP); Chihiro Sugimoto, Hokkaido (JP); Gakunan Gen, Hokkaido (JP); Kimie Kadota, Hokkaido (JP); Noboru Inoue, Hokkaido (JP); Naoaki Yokoyama, Hokkaido (JP); Naotoshi Tsuji, Ibaraki (JP)

(73) Assignees: Meji Seika Kaisha, Ltd., Tokyo (JP); Kozo Fujisaki, Hokkaido (JP)

( * ) Notice: Subject to any disclaimer, the term of this patent is extended or adjusted under 35 U.S.C. 154(b) by 19 days.

(21) Appl. No.: 10/506,047

(22) PCT Filed: Feb. 28, 2003

(86) PCT No.: PCT/JP03/02336

§ 371 (c)(1),
(2), (4) Date: Aug. 30, 2004

(87) PCT Pub. No.: WO03/072781

PCT Pub. Date: Sep. 4, 2003

(65) Prior Publication Data

US 2005/0106677 A1    May 19, 2005

(30) Foreign Application Priority Data

Feb. 28, 2002  (JP) .............................. 2002-053146

(51) Int. Cl.
*C07K 14/00* (2006.01)

(52) U.S. Cl. ..................................................... 530/350
(58) Field of Classification Search ................. None
See application file for complete search history.

(56) References Cited

FOREIGN PATENT DOCUMENTS

WO    WO 03/072609 A1    9/2003

OTHER PUBLICATIONS

Yagi, F. et al. Glycoconjugate Journal 18: 745-749 (2001).*
Astigarraga et al. Veterinary Parasitology 60: 133-147 (1995). "A study of the vaccinal value of various extracts of concealed antigens and salivary gland extracts against Ornithodoros erraticus and Ornithodoros moubata".*
C.A. Hill et al, "EST, Amblyomma Americanum", EMBL-EBI, Oct. 14, 2000, database accession No. BF007251 (XP-002328634).
C.A. Hill et al, "Analysis of the Expressed Genome of the Lone Star Tick, Amblyomma Americanum (Acari: Ixodidae) Using an Expressed Sequence Tag Approach", Microbial & Comparative Genomics, Nov. 2, 2000, pp. 89-101, vol. No. 5 (XP 009047874).
Kovar V. et al., Isolation and characterization of Dorin M., a lectin from plasma of the soft tick, Ornithodoros moubata Insect. Biochem. Mol. Biol., 2000, 30 (3), pp. 195 to 205.
Grubhoffer L. et al., New Lectins of Invertebrates, Zool. Sci., 1991, 8 (6), pp. 1001 to 1003.

* cited by examiner

*Primary Examiner*—Jon Weber
*Assistant Examiner*—Anand Desai
(74) *Attorney, Agent, or Firm*—Sughrue Mion, PLLC

(57) ABSTRACT

A novel galectin, a polynucleotide encoding the same, a vector and a transformant comprising the polynucleotide, an antibody against the galectin, and a screening method for screening a substance capable of modifying the galectin, are disclosed. According to the galectin, polynucleotide, or vector, it is possible, for example, to exterminate ticks, or to treat or prevent tick-borne infections such as rickettsiosis, filariasis, Q fever, African recurrent fever, or viral encephalitis.

10 Claims, 5 Drawing Sheets

F I G. 1
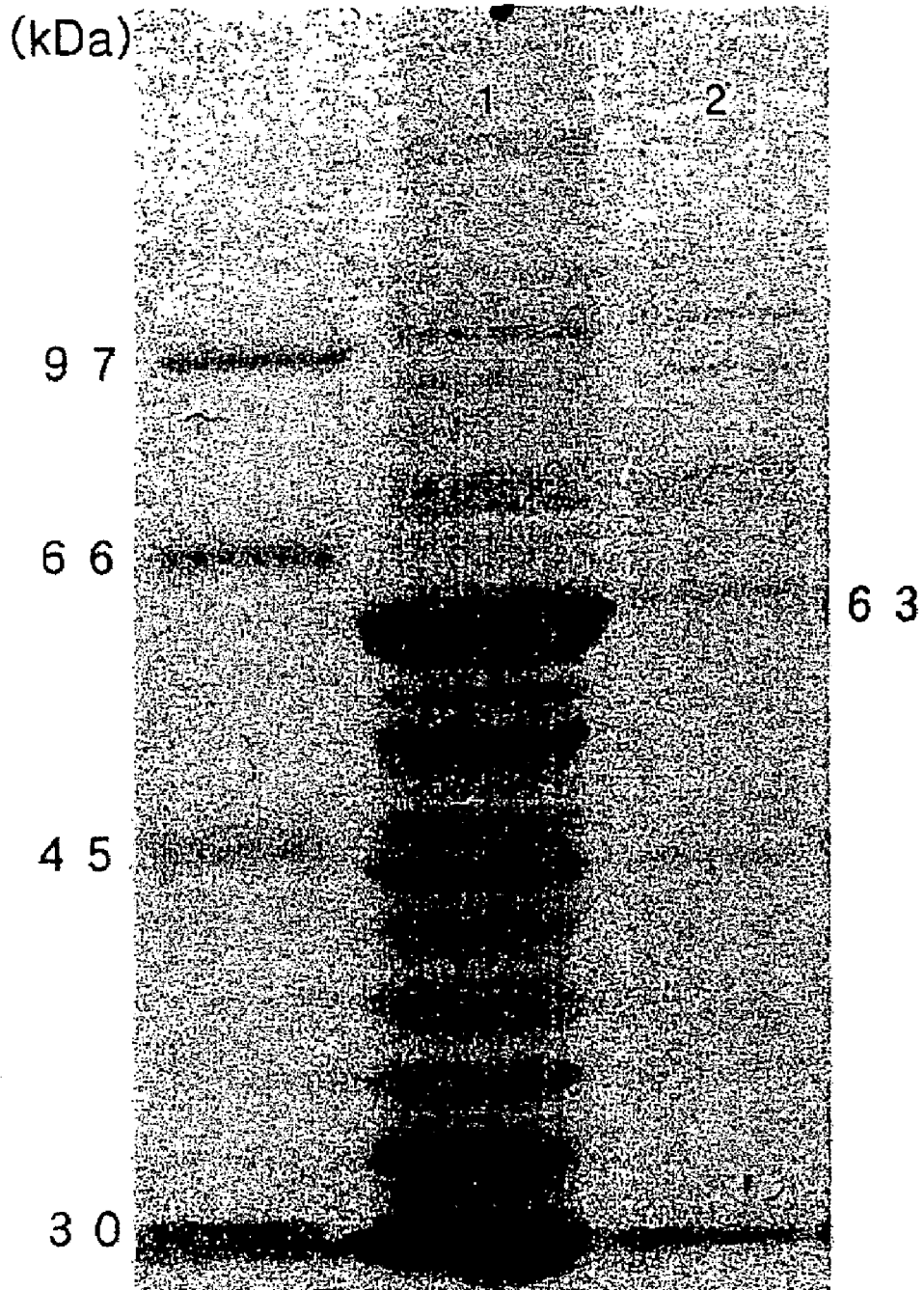

F I G. 4
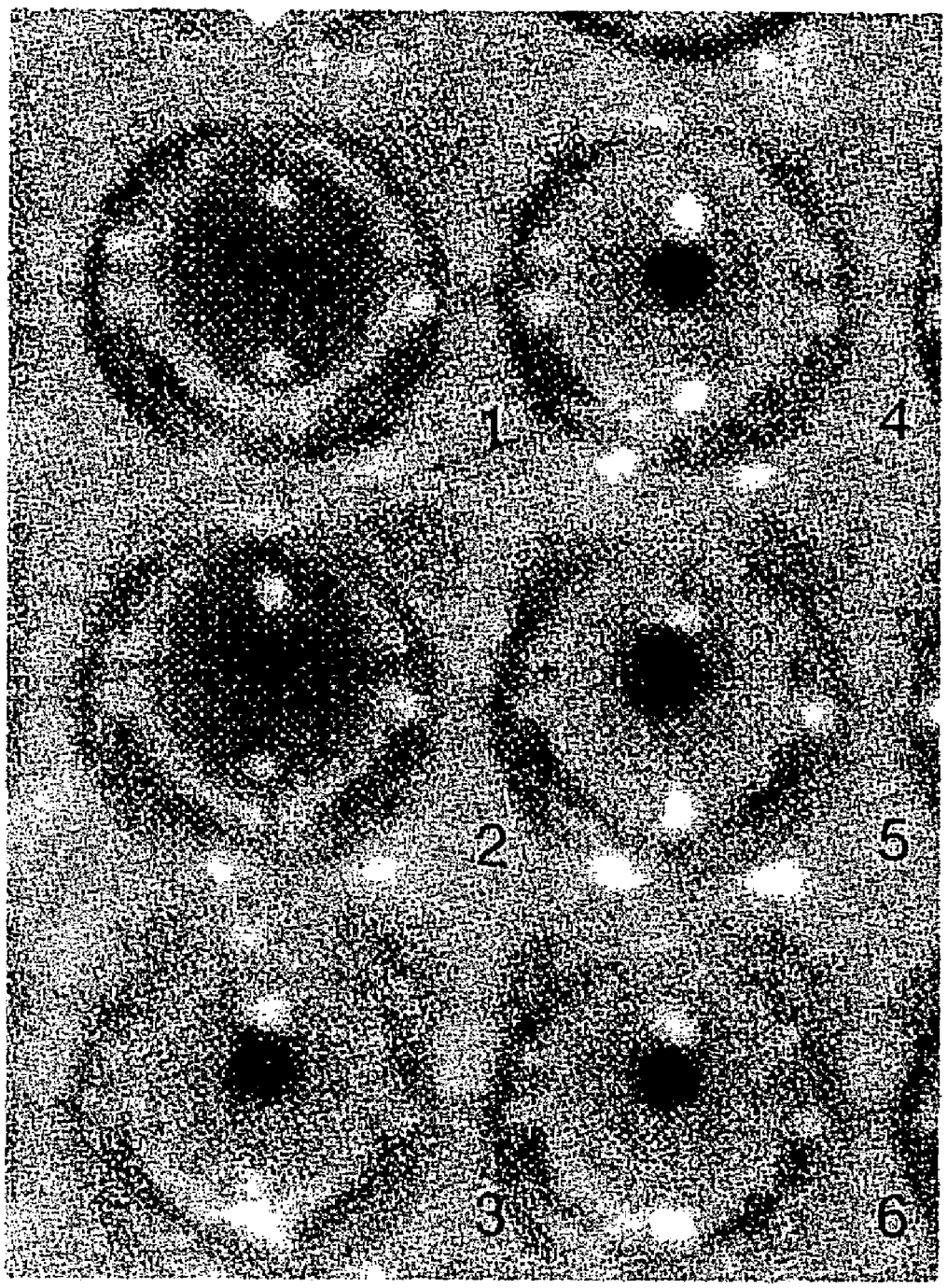

SEQUENCE LISTING

<160> NUMBER OF SEQ ID NOS: 2

<210> SEQ ID NO 1
<211> LENGTH: 1094
<212> TYPE: DNA
<213> ORGANISM: Ornithodoros moubata
<220> FEATURE:
<221> NAME/KEY: CDS
<222> LOCATION: (24)..(1025)

<400> SEQUENCE: 1

```
gctccatctg gctgacttac gcg atg tat cgt atg ccc cct ttt tac ccg gac      53
                        Met Tyr Arg Met Pro Pro Phe Tyr Pro Asp
                         1               5                      10 ccg agt ctg gtc acc tat agc ccg ctg gtc cca gta cgc acc ccc ttg      101
Pro Ser Leu Val Thr Tyr Ser Pro Leu Val Pro Val Arg Thr Pro Leu
                 15                  20                  25 aga act ctc act ccg ggc act gtc att gaa ctg cac gga cgc ata cac      149
Arg Thr Leu Thr Pro Gly Thr Val Ile Glu Leu His Gly Arg Ile His
             30                  35                  40 aat acc aaa agg ttt gcc atc aac ttg gaa act aag gat ggt gat ata      197
Asn Thr Lys Arg Phe Ala Ile Asn Leu Glu Thr Lys Asp Gly Asp Ile
         45                  50                  55 gca ctc cac atc aac ccc cga ttc gac tgc aac cac gtg gtg ctg aac      245
Ala Leu His Ile Asn Pro Arg Phe Asp Cys Asn His Val Val Leu Asn
     60                  65                  70 tcg ttc cgt ggc gga aaa tgg gaa atg gaa gag cat gcg ccc ctc act      293
Ser Phe Arg Gly Gly Lys Trp Glu Met Glu Glu His Ala Pro Leu Thr
 75                  80                  85                  90 att gca cag gga cag gac ttc tct tgc atg atc ctg gtg gaa aaa atg      341
Ile Ala Gln Gly Gln Asp Phe Ser Cys Met Ile Leu Val Glu Lys Met
                 95                 100                 105 gag tac aag atg gcc ttt aat gga caa cat ttg aca tca ttt aag cac      389
Glu Tyr Lys Met Ala Phe Asn Gly Gln His Leu Thr Ser Phe Lys His
            110                 115                 120 cgt ata ctc ttt tca ctc gtt gat gtg ttg acg gtg gat ccc ggc gtt      437
Arg Ile Leu Phe Ser Leu Val Asp Val Leu Thr Val Asp Pro Gly Val
        125                 130                 135 aca gta cac aaa gta gac cag aag cct ccc atg gat gtg agc cct cca      485
Thr Val His Lys Val Asp Gln Lys Pro Pro Met Asp Val Ser Pro Pro
    140                 145                 150 atg cag ata gcg cct tct atg cca cca gga gtt gca cca gcc atg ctc      533
Met Gln Ile Ala Pro Ser Met Pro Pro Gly Val Ala Pro Ala Met Leu
155                 160                 165                 170 ata gga ggg gga atg cca cca cag cct acg atg caa gta atg cct tct      581
Ile Gly Gly Gly Met Pro Pro Gln Pro Thr Met Gln Val Met Pro Ser
                175                 180                 185
```

```
cct gca caa gaa ccc acc ttc aat ccg ccc acg ccg ttc tgc tgt caa       629
Pro Ala Gln Glu Pro Thr Phe Asn Pro Pro Thr Pro Phe Cys Cys Gln
            190                 195                 200 ctg gcc cag ggt tgc tat cct gga ttg ctc atc tac atc agc ggc cgg       677
Leu Ala Gln Gly Cys Tyr Pro Gly Leu Leu Ile Tyr Ile Ser Gly Arg
            205                 210                 215 cct tat gca gaa cct gac agg ttc aac att gac ttg aca tgt gga ccg       725
Pro Tyr Ala Glu Pro Asp Arg Phe Asn Ile Asp Leu Thr Cys Gly Pro
        220                 225                 230 cat gcc gta cct ggg tct ccg gtt gct ttt cac tgg aat ccc cgc ttc       773
His Ala Val Pro Gly Ser Pro Val Ala Phe His Trp Asn Pro Arg Phe
235                 240                 245                 250 tac gag aag tct gtg gtc cgc aac tcc ttc ttg gac gag ggc tgg gga       821
Tyr Glu Lys Ser Val Val Arg Asn Ser Phe Leu Asp Glu Gly Trp Gly
                255                 260                 265 gtg gag gag cga gaa ggc cga ggg ttc cct tac gag gcg ggc gtc cat       869
Val Glu Glu Arg Glu Gly Arg Gly Phe Pro Tyr Glu Ala Gly Val His
            270                 275                 280 ttt gat atg atc att cag gtc ctt cac gac cgc atc aat gtc gca gtt       917
Phe Asp Met Ile Ile Gln Val Leu His Asp Arg Ile Asn Val Ala Val
            285                 290                 295 aat ggg caa cac tat gca gaa ttt cgt cac aga ctt caa ccc att tcg       965
Asn Gly Gln His Tyr Ala Glu Phe Arg His Arg Leu Gln Pro Ile Ser
        300                 305                 310 caa atc act cat ctc cga att gag gga gat gtt gtg att gcc tct gtg      1013
Gln Ile Thr His Leu Arg Ile Glu Gly Asp Val Val Ile Ala Ser Val
315                 320                 325                 330 agg ttc cag tga gagagggcga aaagagatga tatatgttag attgaaaata          1065
Arg Phe Gln tattacatga ggtattctat tcaaaaaaa                                       1094

<210> SEQ ID NO 2
<211> LENGTH: 333
<212> TYPE: PRT
<213> ORGANISM: Ornithodoros moubata

<400> SEQUENCE: 2

Met Tyr Arg Met Pro Pro Phe Tyr Pro Asp Pro Ser Leu Val Thr Tyr
1               5                   10                  15

Ser Pro Leu Val Pro Val Arg Thr Pro Leu Arg Thr Leu Thr Pro Gly
            20                  25                  30

Thr Val Ile Glu Leu His Gly Arg Ile His Asn Thr Lys Arg Phe Ala
        35                  40                  45

Ile Asn Leu Glu Thr Lys Asp Gly Asp Ile Ala Leu His Ile Asn Pro
    50                  55                  60

Arg Phe Asp Cys Asn His Val Val Leu Asn Ser Phe Arg Gly Gly Lys
65                  70                  75                  80

Trp Glu Met Glu Glu His Ala Pro Leu Thr Ile Ala Gln Gly Gln Asp
                85                  90                  95

Phe Ser Cys Met Ile Leu Val Glu Lys Met Glu Tyr Lys Met Ala Phe
            100                 105                 110

Asn Gly Gln His Leu Thr Ser Phe Lys His Arg Ile Leu Phe Ser Leu
        115                 120                 125

Val Asp Val Leu Thr Val Asp Pro Gly Val Thr Val His Lys Val Asp
    130                 135                 140

Gln Lys Pro Pro Met Asp Val Ser Pro Pro Met Gln Ile Ala Pro Ser
145                 150                 155                 160
```

```
Met Pro Pro Gly Val Ala Pro Ala Met Leu Ile Gly Gly Gly Met Pro
                165             170             175

Pro Gln Pro Thr Met Gln Val Met Pro Ser Pro Ala Gln Glu Pro Thr
            180             185             190

Phe Asn Pro Pro Thr Pro Phe Cys Cys Gln Leu Ala Gln Gly Cys Tyr
        195             200             205

Pro Gly Leu Leu Ile Tyr Ile Ser Gly Arg Pro Tyr Ala Glu Pro Asp
    210             215             220

Arg Phe Asn Ile Asp Leu Thr Cys Gly Pro His Ala Val Pro Gly Ser
225             230             235             240

Pro Val Ala Phe His Trp Asn Pro Arg Phe Tyr Glu Lys Ser Val Val
                245             250             255

Arg Asn Ser Phe Leu Asp Glu Gly Trp Gly Val Glu Glu Arg Glu Gly
            260             265             270

Arg Gly Phe Pro Tyr Glu Ala Gly Val His Phe Asp Met Ile Ile Gln
            275             280             285

Val Leu His Asp Arg Ile Asn Val Ala Val Asn Gly Gln His Tyr Ala
    290             295             300

Glu Phe Arg His Arg Leu Gln Pro Ile Ser Gln Ile Thr His Leu Arg
305             310             315             320

Ile Glu Gly Asp Val Val Ile Ala Ser Val Arg Phe Gln
                325             330
```

MITE GALECTIN

TECHNICAL FIELD

This invention relates to a tick galectin.

BACKGROUND ART

Ticks are the cause, directly or indirectly, of extensive damage to animals or humans. Examples of the direct damage are pruritus or bleeding caused by biting or blood-sucking, or tick paralysis or allergic diseases caused by saliva secreted in blood-sucking or regurgitation of midgut contents. Examples of the indirect damage are various diseases in livestock, caused by viruses, rickettsiae, bacterium, spirochaeta, protozoa, nematoda, or the like. This damage causes enormous losses at home and abroad, and threat of emerging and re-emerging zoonotic diseases by ticks is becoming a serious problem.

Under these circumstances, various methods to exterminate ticks are used in many countries. Among these methods, the major one is the use of agents such as organic phosphorus agents, carbamate agents, pyrethroid or macrolide antibiotics, or the like. However, in any agent, a drug resistance is established by using the agent successively or heavily, and thus many agents lose their miticidal activity. Further, when using such agents, it is necessary to take side effects to animals into consideration. In addition, there is a problem of a remnant agent which may threaten the safety of foods and the environment, and people tend to avoid the use of such agents. Furthermore, the use of agents is approaching limitation, with respect to the enormous development cost, in addition to the effectiveness thereof and an applicable area. As described above, it is considered difficult to prevent the parasitism of ticks to humans or animals, and the damage caused by ticks-borne infection in the 21st century, by means of the use of agents.

In hematophagous arthropods including ticks, acquisition of protective immune response against reinfection in a host against a viral or bacterial infection is known and has been confirmed in the laboratory stage [Fujisaki, Nat. Inst. Anim. Hlth. Quart. (Tokyo), 18, 27–38 (1978)]. Due to the recent progress in gene recombination techniques, genes encoding protective antigens, enzymes related to metamorphosis specific to hematophagous arthropods, or the like are being intensively cloned in many countries, and an attempt to manufacture safe vaccine proteins or chemotherapeutic agents has been made.

However, such an agent in practical use is only that against *Boophilus microplus*, which was developed by Willadesen [Willadesen and Jogejan, Prasitology Today. 15, 258–262(1999)]. There is now a search for a vaccine against Ornithodoros moubata, which is widely distributed over Southern Europe and the African continent and mediates zoonotic diseases such as rickettsiosis, filariasis, Q fever, African recurrent fever, or viral encephalitis, and thus the rapid development and practical application of such a vaccine is greatly desired.

Further, although the development and practical application of a vaccine against all ticks is greatly desired, such a vaccine, effective against all ticks, has not been developed. It is considered that the main reason for this is that the breeding of ticks is difficult, and that the search for candidate antigens relating to protective immunity against parasite infestation has not progressed. Under these circumstances, the search for major antigens in Ornithodoros moubata, and the development of an effective recombinant vaccine in which the major antigen or a recombinant protein thereof is used as an antigen, are desired.

From a medical aspect, it is known that galection is overexpressed in an inflammatory tissue or a tumor tissue, and thus galectin is noted as a marker for an inflammation or tumor. Further, it is known that galectin is involved with an apoptosis of T cells or B cells, and plays an important role in self recognition. An attempt to use galectin or an inhibitor thereagainst as an immunosuppressive agent for autoimmune disease, an anti-inflammatory agent, or an antimetastatic agent has been made, and there are great expectations that they can be used as medicaments.

DISCLOSURE OF INVENTION

The present inventors have conducted intensive studies into obtaining a novel polypeptide useful as a candidate for a vaccine against ticks, particularly Ornithodoros moubata, and a polynucleotide encoding the polypeptide and, as a result, found a novel galectin and a polynucleotide encoding the same. Further, the present inventors inoculated the galectin into mice, to observe the induction of an antibody production, and confirmed that the galectin is useful as a tick vaccine. The present invention is based on the above findings.

The object of the present invention is to provide a novel galectin useful as a tick vaccine, and a polynucleotide encoding the galectin.

The object can be solved by a polypeptide of the present invention, i.e., (1) a polypeptide consisting of the amino acid sequence of SEQ ID NO: 2;

(2) a polypeptide comprising the amino acid sequence of SEQ ID NO: 2 and exhibiting a galectin activity;

(3) a polypeptide exhibiting a galectin activity and comprising an amino acid sequence in which one or plural amino acids are substituted, deleted, and/or inserted at one or plural positions in the amino acid sequence of SEQ ID NO: 2; or (4) a polypeptide comprising an amino acid sequence having a 60% or more homology with the amino acid sequence of SEQ ID NO: 2, and exhibiting a galectin activity.

The present invention relates to a polynucleotide encoding the polypeptide.

The present invention relates to a vector comprising the polynucleotide.

The present invention relates to a transformant comprising the polynucleotide.

The present invention relates to a process for producing the polypeptide, comprising the step of culturing the transformant.

The present invention relates to a medicament comprising the polypeptide or a fragment thereof, the polynucleotide, or the vector.

The present invention relates to a pharmaceutical composition comprising the polypeptide or a fragment thereof, the polynucleotide, or the vector, and a pharmaceutically or veterinary acceptable carrier or diluent.

The present invention relates to a method for exterminating ticks, comprising administering to a subject in need thereof the polypeptide or a fragment thereof, the polynucleotide, or the vector in an amount effective therefor.

The present invention relates to a method for treating or preventing a tick-borne infection, comprising administering to a subject in need thereof the polypeptide or a fragment thereof, the polynucleotide, or the vector in an amount effective therefor.

The present invention relates to an antibody or a fragment thereof, which binds to the polypeptide.

The present invention relates to a method for screening a substance capable of modifying a galectin activity of the polypeptide, comprising the steps of:

bringing the polypeptide into contact with a substance to be tested; and analyzing the galectin activity of the polypeptide.

BRIEF DESCRIPTION OF DRAWINGS

FIG. 1 shows the result of electrophoresis of a recombinant galectin fusion protein.

FIG. 4 shows the result of agglutination test of the recombinant galectin fusion protein against mouse erythrocytes.

BEST MODE FOR CARRYING OUT THE INVENTION

Figure 2:
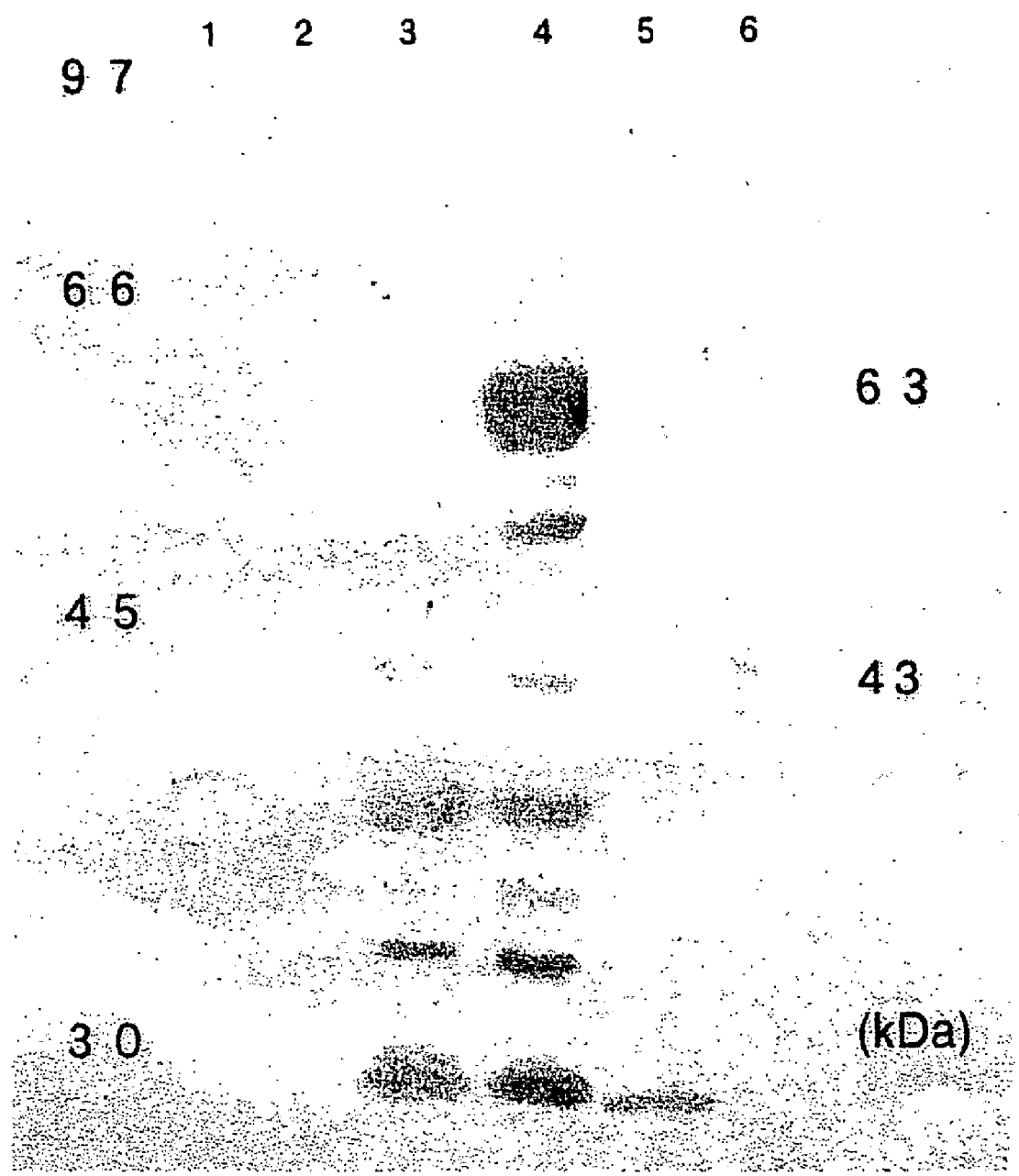
FIG. 2 shows the result of electrophoresis by immunoblotting using a monoclonal antibody against hemolymph from 4th instar nymphs.

The present invention will be explained in detail hereinafter.

[1] Polypeptide of the Present Invention

The polypeptides of the present invention includes
(1) a polypeptide consisting of the amino acid sequence of SEQ ID NO: 2;
(2) a polypeptide comprising the amino acid sequence of SEQ ID NO: 2 and exhibiting a galectin activity;
(3) a polypeptide comprising an amino acid sequence in which one or plural amino acids are substituted, deleted, and/or inserted at one or plural positions in the amino acid sequence of SEQ ID NO: 2, and exhibiting a galectin activity (hereinafter referred to as a variation functionally equivalent); and
(4) a polypeptide comprising an amino acid sequence having a 60% or more homology with the amino acid sequence of SEQ ID NO: 2, and exhibiting a galectin activity (hereinafter referred to as a homologous polypeptide).

The term "galectin activity" as used herein means an activity of binding to the β-galactoside. Whether or not a polypeptide to be tested exhibits the galectin activity may be easily confirmed, for example, by a known method for measuring the galectin activity, in which the polypeptide to be tested is brought into contact with galactose or a derivative thereof, and then the binding between the polypeptide and galactose or a derivative thereof and/or a degree thereof is analyzed. The method is not particularly limited, but is preferably confirmed by a method described in Example 12.

More particularly, for example, a polypeptide to be tested is passed through an affinity column (for example, a lactosyl Sepharose column) carrying galactose or a derivative thereof, and then whether or not the polypeptide to be tested is adsorbed by the column is analyzed. When the polypeptide to be tested is adsorbed by the column, it may be judged that the polypeptide to be tested exhibits the galectin activity. Conversely, when the polypeptide to be tested is not adsorbed by the column, it may be judged that the polypeptide to be tested does not exhibit the galectin activity.

The "polypeptide comprising the amino acid sequence of SEQ ID NO: 2 and exhibiting the galectin activity" as the polypeptide of the present invention includes, for example, a fusion polypeptide consisting of an amino acid sequence in which an appropriate marker sequence or the like is added to the N-terminus and/or the C-terminus of the amino acid sequence of SEQ ID NO: 2, and exhibiting the galectin activity; or a fusion polypeptide of the polypeptide consisting of the amino acid sequence of SEQ ID NO: 2 and a partner for the fusion, and exhibiting the galectin activity.

As the marker sequence, for example, a sequence for easily carrying out a confirmation of polypeptide expression, a confirmation of intracellular localization thereof, a purification thereof, or the like may be used. As the sequence, there may be mentioned, for example, a FLAG tag, a hexa-histidine tag, a hemagglutinin tag, a myc epitope, or the like.

As the partner for fusion, there may be mentioned, for example, a polypeptide for purification [for example, glutathione S-transferase (GST) or a fragment thereof], a polypeptide for detection [for example, hemagglutinin or β-galactosidase α a peptide (LacZ α), or a fragment thereof], a polypeptide for expression (for example, a signal sequence), or the like.

In the above fusion polypeptide, an amino acid sequence which can be specifically digested with a protease such as thrombin or factor Xa may be optionally inserted between the polypeptide consisting of the amino acid sequence of SEQ ID NO: 2 and the marker sequence or the partner for fusion.

The variation functionally equivalent of the present invention is not particularly limited, so long as it is a polypeptide comprising an amino acid sequence in which one or plural (preferably 1 to 10, more preferably 1 to 7, most preferably 1 to 5) amino acids in total (for example, one to several amino acids in total) are deleted, substituted, and/or inserted at one or plural positions in the amino acid sequence of SEQ ID NO: 2, and exhibiting the galectin activity. Further, an origin of the variation functionally equivalent is not limited to Ornithodoros moubata.

The variation functionally equivalent of the present invention includes not only Ornithodoros moubata variations of the polypeptide consisting of the amino acid sequence of SEQ ID NO: 2, but also variations functionally equivalent derived from organisms other than Ornithodoros moubata [for example, Argasids (soft ticks) other than Ornithodoros moubata or, or Ixodids (hard ticks)]. Further, it includes polypeptides prepared using polynucleotides obtained by artificially modifying their amino acid sequences encoded thereby by genetic engineering techniques, on the basis of polynucleotides encoding these native polypeptides (i.e., Ornithodoros moubata variations or variations functionally equivalent derived from organisms other than Ornithodoros moubata), or on the basis of polynucleotides encoding the amino acid sequence of SEQ ID NO: 2. The term "variation" as used herein means an individual difference between the same polypeptides in the same species or a difference between homologous polypeptides in several species.

Ornithodoros moubata variations of the polypeptide consisting of the amino acid sequence of SEQ ID NO: 2, or variations functionally equivalent derived from organisms other than Ornithodoros moubata may be obtained by those skilled in the art in accordance with the information of a base sequence (for example, the base sequence of the 24th to 1025th bases in the base sequence of SEQ ID NO: 1) of a polynucleotide encoding the polypeptide consisting of the amino acid sequence of SEQ ID NO: 2. In this connection, genetic engineering techniques may be generally performed in accordance with known methods (for example, Sambrook et al., "Molecular Cloning, A Laboratory Manual", Cold Spring Harbor Laboratory Press, 1989), unless otherwise specified.

For example, an appropriate probe or appropriate primers are designed in accordance with the information of a base sequence of a polynucleotide encoding the polypeptide consisting of the amino acid sequence of SEQ ID NO: 2. A polymerase chain reaction (PCR) method (Saiki, R. K. et al., Science, 239, 487–491, 1988) or a hybridization method is carried out using a sample (for example, total RNA or an mRNA fraction, a cDNA library, or a phage library) derived prepared from an organism [for example, Argasids (soft ticks) other than Ornithodoros moubata or, or Ixodids (hard ticks)] of interest and the primers or the probe to obtain a polynucleotide encoding the polypeptide. A desired polypeptide may be obtained by expressing the resulting polynucleotide in an appropriate expression system and confirming that the expressed polypeptide exhibits the galectin activity by, for example, the method described in Example 6.

Further, the polypeptide artificially modified by genetic engineering techniques may be obtained by, for example, the following procedure. A gene encoding the polypeptide is obtained by a conventional method such as site-specific directed mutagenesis (Mark, D. F. et al., Proc. Natl. Acad. Sci. USA, 81, 5662–5666, 1984). A desired polypeptide may be obtained by expressing the resulting polynucleotide in an appropriate expression system and confirming that the expressed polypeptide exhibits the galectin activity by, for example, the method described in Example 6.

The homologous polypeptide of the present invention is not particularly limited, so long as it is a polypeptide having an amino acid sequence having a 60% or more homology with the amino acid sequence of SEQ ID NO: 2, and exhibiting the galectin activity. The homologous polypeptide of the present invention may have an amino acid sequence having preferably a 70% or more homology, more preferably a 80% or more homology, more preferably a 90% or more homology, more preferably a 95% or more homology, most preferably a 98% or more homology, with respect to the amino acid sequence of SEQ ID NO: 2. The term "homology" as used herein means a value obtained by a Clustal program (Higgins and Sharp, Gene, 73, 237–244, 1988; and Thompson et al., Nucleic Acid Res., 22, 4673–4680, 1994) in accordance with a default parameter.

The above-mentioned novel polypeptide of the present invention may be manufactured by various known methods, for example, known genetic engineering techniques using the polynucleotide of the present invention which encodes the polypeptide of the present invention. More particularly, the polypeptide of the present invention may be prepared by culturing the transformant of the present invention described below (i.e., the transformant comprising the polynucleotide of the present invention) under conditions in which the novel polypeptide of the present invention can be expressed, and then separating and purifying the desired polypeptide from the resulting culture in accordance with a conventional method for a polypeptide separation and purification. As the separation and purification method, there may be mentioned, for example, salting-out with ammonium sulfate, an ion exchange column chromatography using ion exchange cellulose, a molecular sieve column chromatography using molecular sieve gel, an affinity column chromatography using protein A agarose, dialysis, lyophilization, or the like.

The present invention includes a fragment of the polypeptide of the present invention. The fragment of the present invention is useful as an active ingredient for the medicament of the present invention or as an antigen for preparing the antibody of the present invention.

[2] Polynucleotide of the Present Invention

The polynucleotide of the present invention is not particularly limited, so long as it encodes the polypeptide of the present invention. As the polynucleotide of the present invention, there may be mentioned, for example, a polynucleotide consisting of the 24th to 1025th bases in the base sequence of the SEQ ID NO: 1. In this connection, the term "polynucleotide" as used herein includes both DNA and RNA.

The present invention includes a polynucleotide comprising a base sequence which can hybridize with the polynucleotide of the present invention, preferably a polynucleotide consisting of a base sequence which can hybridize with the polynucleotide of the present invention. The base sequence capable of hybridizing with the polynucleotide of the present invention is preferably a base sequence complementary to the base sequence (or a partial sequence thereof) of the polynucleotide of the present invention, more preferably a base sequence complementary to the base sequence (or a partial sequence thereof) consisting of the 24th to 1025th bases in the base sequence of the SEQ ID NO: 1.

[3] Vector and Transformant of the Present Invention

The vector of the present invention is not particularly limited, so long as it comprises the polynucleotide of the present invention. As the vector, there may be mentioned, for example, a vector obtained by introducing the polynucleotide of the present invention into a known expression vector appropriately selected in accordance with a host cell to be used.

The transformant of the present invention is not particularly limited, so long as it comprises the polynucleotide of the present invention. The transformant of the present invention may be, for example, a cell in which the polynucleotide is integrated into a chromosome of a host cell, or a transformant containing the polynucleotide as a vector comprising polynucleotide. Further, the transformant of the present invention may be a transformant expressing the polypeptide of the present invention, or a transformant not expressing the polypeptide of the present invention. The transformant of the present invention may be obtained by, for example, transfecting a desired host cell with the vector of the present invention or the polynucleotide of the present invention per se.

The host cell may be, for example, a known microorganism usually used, for example, an *Escherichia coli* or yeast (*Saccharomyces cerevisiae*), or a known cultivated cell, such as an animal cell, such as a CHO cell, an HEK-293 cell, or a COS cell, or an insect cell such as a BmN4 cell.

The known expression vector may be, for example, pUC, pTV, pGEX, pKK, or pTrcHis for an *Escherichia coli*; pEMBLY or pYES2 for the yeast; pcDNA3 or pMAMneo for the CHO cell; pcDNA3 for the HEK-293 cell; pcDNA3 for the COS cell; a vector (such as pBK283) containing a polyhedrin promoter of a silkworm nucleopolyhederovirus (BmNPV) for the BmN4 cell. Further, the expression vector includes a virus vector which can be used as a vector for a gene therapy, such as retrovirus, adenovirus, or Sendai virus.

[4] Medicament of the Present Invention

The medicament of the present invention (preferably a tick vaccine) comprises, as a active ingredient, the polypeptide of the present invention or a fragment thereof, the polynucleotide of the present invention, or the vector of the present invention. In the present invention, the polypeptide of the present invention or a fragment thereof, the polynucleotide of the present invention, or the vector of the present invention can be orally or parenterally administered alone, or preferably together with a pharmaceutically or veterinarily acceptable carrier or diluent, to an animal (preferably a mammal, particularly a human) in need of an extermination of ticks.

When the active ingredient in the medicament of the present invention (i.e., the polypeptide of the present invention or a fragment thereof, the polynucleotide of the present invention, or the vector of the present invention) is administered to an animal as a tick vaccine, an antibody production may be induced and then ticks may be terminated by development of protective immunity against reinfection in the host animal. Further, as a result, it is possible to treat or prevent tick-borne infections such as rickettsiosis, filariasis, Q fever, African recurrent fever, or viral encephalitis.

In other words, the pharmaceutical composition (preferably pharmaceutical composition for exterminating ticks or pharmaceutical composition for treating or preventing a tick-borne infection) of the present invention comprises the polypeptide of the present invention or a fragment thereof, the polynucleotide of the present invention, or the vector of the present invention as the active ingredient, and a pharmaceutically or veterinary acceptable carrier or diluent. The active ingredient in the present invention (i.e., the polypeptide of the present invention or a fragment thereof, the polynucleotide of the present invention, or the vector of the present invention) can be used in the manufacture of the above medicament (preferably medicament for exterminating ticks or medicament for treating or preventing a tick-borne infection).

When the medicament of the present invention is used as a tick vaccine, the fragment of the polypeptide of the present invention is not particularly limited, so long as the fragment administered to a subject can induce immunity thereagainst. The fragment can be appropriately selected by those skilled in the art.

The medicament (particularly the tick vaccine) of the present invention can be used, for example, by mixing the polypeptide of the present invention with an adjuvant or the like and inoculating the resulting mixture into an animal (for example, livestock) at an appropriate interval as a tick vaccine. Further, it can be used by dissolving or suspending the polypeptide of the present invention directly in an appropriate solvent, or by enclosing it in liposomes or integrating a DNA encoding it in an appropriate vector. Furthermore, it can be used in an appropriate formulation such as injections, tablets, capsules, eye drops, creams, suppositories, sprays, poultices, or the like, optionally by adding a pharmaceutical acceptable carrier to the polypeptide of the present invention.

As the pharmaceutical acceptable carrier, well-known solvents, bases, stabilizing agents, antiseptics, solubilizing agents, fillers, buffers, and the like may be used. When the polypeptide of the present invention contained in the medicament of the present invention is used in the above formulation, the administration method and the dose may be determined in accordance with, for example, the age or sex of each subject, or the kind or degree of each disease.

The oral administration includes a sublingual administration. As the parenteral administration, for example, inhalation, percutaneous administration, ophthalmic administration, vaginal administration, intra-articular administration, rectal administration, intra-arterial administration, intravenous administration, local administration, intramuscular administration, subcutaneous administration, intraperitoneal administration, or the like may be selected.

It is known that galection is overexpressed in an inflammatory tissue or a tumor tissue, and that galectin is involved with apoptosis of T cells or B cells and plays an important role in self recognition [H. Leffler, Trends in Glycoscience and Glycotechnology, 6, 9–19(1997)]. Therefore, the polypeptide of the present invention, the polynucleotide of the present invention, the vector of the present invention, the antibody or a fragment thereof of the present invention, or a substance capable of modifying (for example, suppressing or promoting) the galectin activity, which can be obtained by the screening method of the present invention, is useful as an active ingredient for an immunosuppressive agent for autoimmune disease, an anti-inflammatory agent, an anti-metastatic agent, or an agent for inducing or suppressing apoptosis.

The present invention includes an immunosuppressive agent for autoimmune disease, an anti-inflammatory agent, an antimetastatic agent, or an agent for inducing or suppressing apoptosis comprising, as an active ingredient, the polypeptide of the present invention, the polynucleotide of the present invention, the vector of the present invention, the antibody or a fragment thereof of the present invention, or a substance capable of modifying (for example, suppressing or promoting) the galectin activity, which can be obtained by the screening method of the present invention.

[5] Antibody and the Fragment Thereof of the Present Invention

An antibody, such as a polyclonal antibody or a monoclonal antibody, which reacts with the polypeptide of the present invention may be obtained by directly administering the polypeptide of the present invention or a fragment thereof to various animals. Alternatively, it may be obtained by a DNA vaccine method (Raz, E. et al., Proc. Natl. Acad. Sci. USA, 91, 9519–9523, 1994; or Donnelly, J. J. et al., J. Infect. Dis., 173, 314–320, 1996), using a plasmid into which a polynucleotide encoding the polypeptide of the present invention is inserted.

The polyclonal antibody may be produced from a serum or eggs of an animal such as a rabbit, a rat, a goat, or a chicken, in which the animal is immunized and sensitized by the polypeptide of the present invention or a fragment thereof emulsified in an appropriate adjuvant (for example, Freund's complete adjuvant) by intraperitoneal, subcutaneous, or intravenous administration. The polyclonal antibody may be separated and purified from the resulting serum or eggs in accordance with conventional methods for polypeptide isolation and purification. Examples of the separation and purification methods include, for example, centrifugal separation, dialysis, salting-out with ammonium sulfate, or a chromatographic technique using such as DEAE-cellulose, hydroxyapatite, protein A agarose, and the like.

The monoclonal antibody may be easily produced by those skilled in the art, according to, for example, a cell fusion method of Kohler and Milstein (Kohler, G. and Milstein, C., Nature, 256, 495–497, 1975).

A mouse is immunized intraperitoneally, subcutaneously, or intravenously several times at an interval of a few weeks by a repeated inoculation of emulsions in which the polypeptide of the present invention or a fragment thereof is emulsified into a suitable adjuvant such as Freund's complete adjuvant. Spleen cells are removed after the final immunization, and then fused with myeloma cells to prepare hybridomas.

As a myeloma cell for obtaining a hybridoma, a myeloma cell having a marker such as a deficiency in hypoxanthine-guanine phosphoribosyltransferase or thymidine kinase (for example, mouse myeloma cell line P3X63Ag8.U1) may be used. As a fusing agent, polyethylene glycol may be used. As a medium for preparation of hybridomas, for example, a commonly used medium such as an Eagle's minimum essential medium, a Dulbecco's modified minimum essential medium, or an RPMI-1640 medium may be used by adding properly 10 to 30% of a fetal bovine serum. The fused strains may be selected by a HAT selection method. A culture supernatant of the hybridomas is screened by a well-known method such as an ELISA method or an immunohistological method, to select hybridoma clones secreting the antibody of interest. The monoclonality of the selected hybridoma is guaranteed by repeating subcloning by a limiting dilution method. Antibodies in an amount which may be purified are produced by culturing the resulting hybridomas in a medium for 2 to 4 days, or in the peritoneal cavity of a pristane-pretreated BALB/c strain mouse for 10 to 20 days.

The resulting monoclonal antibodies in the culture supernatant or the ascites may be separated and purified by conventional polypeptide isolation and purification methods. Examples of the separation and purification methods include, for example, centrifugal separation, dialysis, salting-out with ammonium sulfate, or chromatographic technique using such as DEAE-cellulose, hydroxyapatite, protein A agarose, and the like.

Further, the monoclonal antibodies or the antibody fragments containing a part thereof may be produced by inserting the whole or a part of a gene encoding the monoclonal antibody into an expression vector and introducing the resulting expression vector into appropriate host cells (such as *E. coli*, yeast, or animal cells).

Antibody fragments comprising an active part of the antibody such as F(ab')$_2$, Fab, Fab', or Fv may be obtained by a conventional method, for example, by digesting the separated and purified antibodies (including polyclonal antibodies and monoclonal antibodies) with a protease such as pepsin, papain, and the like, and separating and purifying the resulting fragments by standard polypeptide isolation and purification methods.

Further, an antibody which reacts to the polypeptide of the present invention may be obtained in a form of single chain Fv or Fab in accordance with a method of Clackson et al. or a method of Zebedee et al. (Clackson, T. et al., Nature, 352, 624–628, 1991; or Zebedee, S. et al., Proc. Natl. Acad. Sci. USA, 89, 3175–3179, 1992). Furthermore, a humanized antibody may be obtained by immunizing a transgenic mouse in which mouse antibody genes are substituted with human antibody genes (Lonberg, N. et al., Nature, 368, 856–859, 1994).

[6] Screening Method of the Present Invention

It is possible to determine whether or not a substance to be tested modifies (for example, suppresses or promotes) the galectin activity of the polypeptide according to the present invention, using the polypeptide of the present invention.

Substances to be tested to which may be applied the screening method of the present invention are not particularly limited, but there may be mentioned, for example, various known compounds (including peptides) registered in chemical files, compounds obtained by combinatorial chemistry techniques (Terrett, N. K. et al., Tetrahedron, 51, 8135–8137, 1995), or random peptides prepared by employing a phage display method (Felici, F. et al., J. Mol. Biol., 222, 301–310, 1991) or the like. In addition, culture supernatants of microorganisms, natural components derived from plants or marine organisms, or animal tissue extracts may be used as the test substances for screening. Further, compounds (including peptides) obtained by chemically or biologically modifying compounds (including peptides) selected by the screening method of the present invention may be used.

The screening method of the present invention may be carried out by a method similar to the above-mentioned method for confirming the galectin activity, except that the polypeptide of the present invention, galactose or a derivative thereof, and the test substance are brought into contact with each other instead of bringing the test polypeptide into contact with galactose or a derivative thereof.

Namely, in the screening method of the present invention, it is confirmed whether or not the test substance modifies the galectin activity of the polypeptide of the present invention by bringing into contact the polypeptide of the present invention, galactose or a derivative thereof, and the test substance, and then analyzing whether or not the polypeptide of the present invention binds to galactose or a derivative thereof (or a degree of the binding) in the presence of the test substance. When the polypeptide of the present invention does not bind to galactose or a derivative thereof, or the degree of the binding is decreased, it is possible to confirm that the test substance suppresses the galectin activity of the polypeptide of the present invention. Alternatively, when the degree of the binding between the polypeptide of the present invention and galactose or a derivative thereof is increased, it is possible to confirm that the test substance promotes the galectin activity of the polypeptide of the present invention.

EXAMPLES

The present invention now will be further illustrated by, but is by no means limited to, the following Examples. The procedures described in the following Examples were performed in accordance with various techniques commonly used in molecular biology, acarology, arthropodology, immunology, or biochemistry, described in, for example, Sambrook et al., "Molecular Cloning, A Laboratory Manual", Cold Spring Harbor Laboratory Press, 1989 or similar books. As a software for analyzing DNA, MacVector™ (Oxford Molecular) was used.

Example 1

Preparation of Hybridoma Producing Anti-Tick Hemolymph Monoclonal Antibody

Hemolymph was collected from Ornithodoros moubata 4th instar nymphs after 6 days from engorgement, and the homogenate thereof was sonicated to obtain a hemolymph solution. After 200 μL of the hemolymph solution (100 μg as a protein amount) was mixed with 200 μL of a complete Freund's adjuvant (Adjuvant Complete Freund; Difco), the mixture was intraperitoneally inoculated into a 7-week-old female BALB/c mouse. After 14, 21, 28, 42, and 56 days from the intraperitoneal inoculation, 200 μL of the hemolymph solution (100 μg as a protein amount) was mixed with an incomplete Freund's adjuvant (Adjuvant Incomplete Freund; Difco), and each booster inoculation was carried out. After 74 days from the intraperitoneal inoculation, the final inoculation with 200 μL of the hemolymph solution (100 μg as a protein amount) was carried out from tail vein. After 3 days, the spleen was removed from the mouse.

The obtained spleen cells and SP2/0-Ag14 myeloma cells were fused using polyethylene glycol. The fused cells were cultured in a GIT medium containing 5% fetal bovine serum (FBS)/5% BriClone (Arch Port Ltd., Dublin, Ireland)/HAT at 37° C. under conditions of 5% $CO_2$. Using the supernatant of each culture, clones producing an antibody were screened by an indirect fluorescent antibody (IFA) method in which the hemolymph from Ornithodoros moubata 4th instar nymphs after 6 days from engorgement was used as an antigen, 10% sodium dodecyl sulfate (SDS)-polyacrylamide gel electrophoresis [Laemmli et al., Nature, 227, 680–685 (1970)], and a western blotting method using immunoblotting [Towbin et al., Proc. Natl. Acad. Sci. USA, 76, 4350–4354 (1979)]. The screening and limiting dilution were repeated until obtaining a single clone, to obtain hybridoma cells producing a monoclonal antibody against the hemolymph from Ornithodoros moubata 4th instar nymphs after 6 days from engorgement.

Example 2

Isolation of Gene n4E12-2 Encoding Novel Tick Galectin

Total RNA was extracted from Ornithodoros moubata 4th instar nymphs after 6 days from engorgement by an Acid Guanidinium-phenol-chloroform method [Chomczynski et al., Anal. Biochem., 162, 156–159 (1987)]. From the resulting total RNA, poly $A^+$ RNA was purified using an mRNA isolation kit [Oligotex-dT30 (Super), code W9021B; Takara] in accordance with a protocol attached to the kit.

The following procedures, i.e., construction of a cDNA library, immunoscreening, and insertion into plasmid of a cDNA clone (in vivo Excision) were performed using commercially available reagent kits (Stratagen) in accordance with protocols attached thereto.

More particularly, cDNA was synthesized using 5 ug of Ornithodoros moubata mRNA as a template and a cDNA synthesis kit (ZAP-cDNA Synthesis Kit, Cat. No. 200401-5; Stratagen). The resulting cDNA was fractionated by a size fractionation with a Sepharose CL-2B gel column, inserted into a vector (Uni-ZAP XR Vector, Cat. No. 237211; Stratagen), and packaged using a packaging reagent (GigapackIII Gold packaging extract; Stratagen). Escherichia coli (E. coli XL1-Blue MRF' strain) was transfected with the packaged product to obtain a library containing approximately 500,000 cDNA clones.

The cDNA library was immunoscreened using the monoclonal antibody obtained in Example 1 against the hemolymph from Ornithodoros moubata 4th instar nymphs after 6 days from engorgement, to obtain three overlapping positive clones. These clones were inserted into plasmid (i.e., converted into a pBluescript) by an in vivo Excision method.

Each plasmid containing a cDNA fragment was purified using a plasmid purification kit (Cat no. 12125; Qiagen), and then PCR was carried out using a sequencing kit (Dye Primer Cycle Sequencing Kit, Part No. 4303153; Perkin Elmer) in accordance with a protocol attached to the kit. Each resulting PCR product was analyzed with a DNA sequencer (ABI PRISM 3100 Genetic Analyzer; Perkin Elmer) to determine a base sequence of each cDNA fragment.

As a result, it was found that all three clones were derived from a single gene. The longest clone was used in the following analyses.

The full length of the cDNA was 1094 bp, and the base sequence thereof was that of SEQ ID NO: 1. It was confirmed that the base sequence contains an open reading frame consisting of 1002 bp (a base sequence consisting of the 24th to 1025th bases in the base sequence of SEQ ID NO: 1). The amino acid sequence of a protein deduced from the open reading frame was the amino acid sequence of SEQ ID NO: 2 consisting of 333 amino acid residues, and the deduced molecular weight was 36.6 kDa.

Hereinafter, the gene is referred to as an n4E12-2 gene. The homology search of the amino acid sequence deduced from the n4E12-2 gene was carried out by a BLAST method (Basic local alignment search tool; Altschul, S. F. et al., J. Mol. Biol., 215, 403–410, 1990; obtained from the National Center for Biotechnology Information). As a result, it was confirmed that the amino acid sequence had a high homology with a known galectin protein. For example, it had an approximately 27% homology with mouse prostatic cancer antigen galectin.

Hereinafter, the protein encoded by the n4E12-2 gene is referred to as "galectin". In this connection, it was confirmed in Examples 11 and 12 that the protein was galectin.

Example 3

Construction of Vector for Expressing Tick Galectin Fusion Protein

The pBluescript plasmid obtained in Example 2, in which the cDNA fragment containing the Ornithodoros moubata n4E12-2 gene was inserted thereinto, was digested with restriction enzymes EcoRI and XhoI. The resulting cDNA fragment containing the n4E12-2 gene was inserted between the EcoRI site and the XhoI site of a vector pGEMEX-4T-3 (Promega) for expression in Escherichia coli, and then recombinant clones in which the galectin ORF fragment was inserted in the same direction as that of glutathione S-transferase (GST) in the vector were selected. A recombinant plasmid pGEMEX-4T-3/n4E12-2 was purified using a plasmid purification kit (Qiagen).

Example 4

Expression of Tick Galectin Recombinant Protein in Escherichia coli

Escherichia coli JM109 (DE3) (Promega) was transformed with the recombinant plasmid prepared in Example 3, and then the transformants were cultured in an LB medium containing ampicillin at 37° C. When $OD_{600nm}$ of the culture became 0.3~0.5, isopropyl-thio-galactoside (IPTG) was added to the culture so that the final concentration became 0.01 mmol/L, and then the transformants were further cultured for 4 hours.

The expression of tick galectin recombinant protein was confirmed by carrying out 10% SDS-polyacrylamide gel electrophoresis [Laemmli et al., Nature, 227, 680–685 (1970)] followed by immunoblotting [Towbin et al., Proc. Natl. Acad. Sci. USA, 76, 4350–4354 (1979)], and then an amido black staining.

As a result, the expression of the recombinant protein having a molecular weight of approximately 63 kDa was observed, and it was confirmed that the recombinant protein was a fusion protein of a GST leader protein (26 kDa) and the tick galectin protein (36.6 kDa) (see FIG. 1).

Example 5

Purification of Tick Galectin Recombinant Protein and Preparation of Antiserum

The recombinant galectin fusion protein expressed in *Escherichia coli* by the method described in Example 4 was purified in accordance with a protocol attached to a commercially available kit (Bulk GST Purification Module; Amersham Bioscience). More particularly, *Escherichia coli* induced with IPTG was collected by centrifugation. The resulting pellet was sonicated in a TNE buffer containing lysozyme, and then the whole was centrifuged at 5000 rpm to obtain the pellet. The resulting pellet (insoluble fraction) was solubilized with Triton X-100, and then the whole was centrifuged at 5000 rpm to obtain the supernatant. The resulting supernatant was mixed with a glutathione resin, and then the mixture was centrifuged at 5000 rpm. The resulting pellet was eluted with 16 mmol/L glutathione solution to purify a "soluble fraction".

The result of electrophoresis of the purified recombinant galectin fusion protein is shown in FIG. 1. In this connection, the electrophoresis, blotting, and staining were performed in the manner similar to that described in Example 4. In FIG. 1, the lane on the left side is the result of molecular weight markers, lane 1 is the result of the insoluble fraction, and lane 2 is the result of the soluble fraction. The number "63" at the right side of lane 2 means the molecular weight (63 kDa) of the recombinant galectin fusion protein.

An emulsion was prepared by mixing 50 µL of a solution containing 100 µg of the purified recombinant galectin fusion protein with 50 µL of a complete Freund's adjuvant (Adjuvant Complete Freund; Difco). The emulsion was intraperitoneally inoculated into a 6-week-old female BALB/c mouse. After 2, 4, 6, and 8 weeks from the intraperitoneal inoculation, 100 µg of the recombinant galectin fusion protein was mixed with 50 uL of Titer Max (Gold; CytRx), and each booster inoculation was carried out. After 2 weeks from the final inoculation, blood was collected and the resulting serum was kept at −30° C.

Example 6

Identification of Native (Wild Type) Galectin by Immunoblotting Using Anti-Tick Hemolymph Monoclonal Antibody In this Example, the wild type galectin protein was identified by immunoblotting [Towbin et al., Proc. Natl. Acad. Sci. USA, 76, 4350–4354 (1979)] using the monoclonal antibody obtained in Example 1 against the hemolymph from Ornithodoros moubata 4th instar nymphs after 6 days from engorgement. As samples, the hemolymph from Ornithodoros moubata 4th instar nymphs after 6 days from engorgement prepared in the manner similar to that described in Example 1 and a lysate of a tick fat body were used. The lysate was prepared by dissecting ticks in PBS (phosphate buffer), homogenizing the obtained tracheae containing the fat body in PBS, and sonicating the homogenate while cooling with ice.

The result is shown in lanes 5 and 6 in FIG. 2. In this connection, lanes 1 to 4 shows the result obtained in Example 7.

In FIG. 2, lane 5 is the result of the hemolymph from Ornithodoros moubata 4th instar nymphs after 6 days from engorgement, and lane 6 is the result of the fat body lysate. The numbers "63" and "43" at the side of lane 6 mean the molecular weight (63 kDa) of the recombinant galectin fusion protein and the molecular weight (43 kDa) of the wild type galectin protein, respectively.

As shown in lanes 5 and 6 in FIG. 2, the specific band of 43 kDa was detected in the hemolymph from Ornithodoros moubata 4th instar nymphs after 6 days from engorgement and the fat body lysate. The reason why the measured molecular weight of the wild type galectin protein is higher than the theoretical molecular weight (36.6 kDa) seems to be due to a difference of a post-translational modification.

Example 7

Confirmation of Reactivity of Anti-Tick Hemolymph Monoclonal Antibody with Respect to Recombinant Galectin Fusion Protein In this Example, the reactivity of the monoclonal antibody obtained in Example 1 against the hemolymph from Ornithodoros moubata 4th instar nymphs after 6 days from engorgement, with respect to the recombinant galectin fusion protein was examined by immunoblotting. As samples, the soluble and insoluble fractions derived from *Escherichia coli* transformed with plasmid pGEMEX-4T-3/n4E12-2 and expressing the recombinant galectin fusion protein (see Example 5), and soluble and insoluble fractions derived from *Escherichia coli* transformed with vector pGEMEX-4T-3 and expressing the GST protein were used.

The result is shown in lanes 1 to 4 in FIG. 2.

In FIG. 2, lanes 1 and 2 are the results of the soluble and insoluble fractions derived from *Escherichia coli* transformed with vector pGEMEX-4T-3 and expressing the GST protein, respectively, and lanes 3 and 4 are the results of the soluble and insoluble fractions derived from *Escherichia coli* transformed with plasmid pGEMEX-4T-3/n4E12-2 and expressing the recombinant galectin fusion protein. As shown in lane 4 in FIG. 2, it was confirmed that the recombinant galectin fusion protein (approximately 63 kDa) reacted with the monoclonal antibody against the hemolymph from Ornithodoros moubata 4th instar nymphs after 6 days from engorgement. It was shown from the result that the recombinant galectin fusion protein is one of the candidates for a tick vaccine. In this connection, the normal mouse serum did not react with the recombinant galectin fusion protein.

Example 8

Identification of Native (Wild Type) Galectin by Immunoblotting Using Anti-Recombinant Galectin Fusion Protein Mouse Serum In this Example, the wild type galectin protein was identified by immunoblotting [Towbin et al., Proc. Natl. Acad. Sci. USA, 76, 4350–4354 (1979)] using the anti-recombinant galectin fusion protein mouse serum obtained in Example 5. As samples, the hemolymph from Ornithodoros moubata 4th instar nymphs after 6 days from engorgement and the fat body lysate, which were the same as those used in Example 6, were used.

Figure 3:
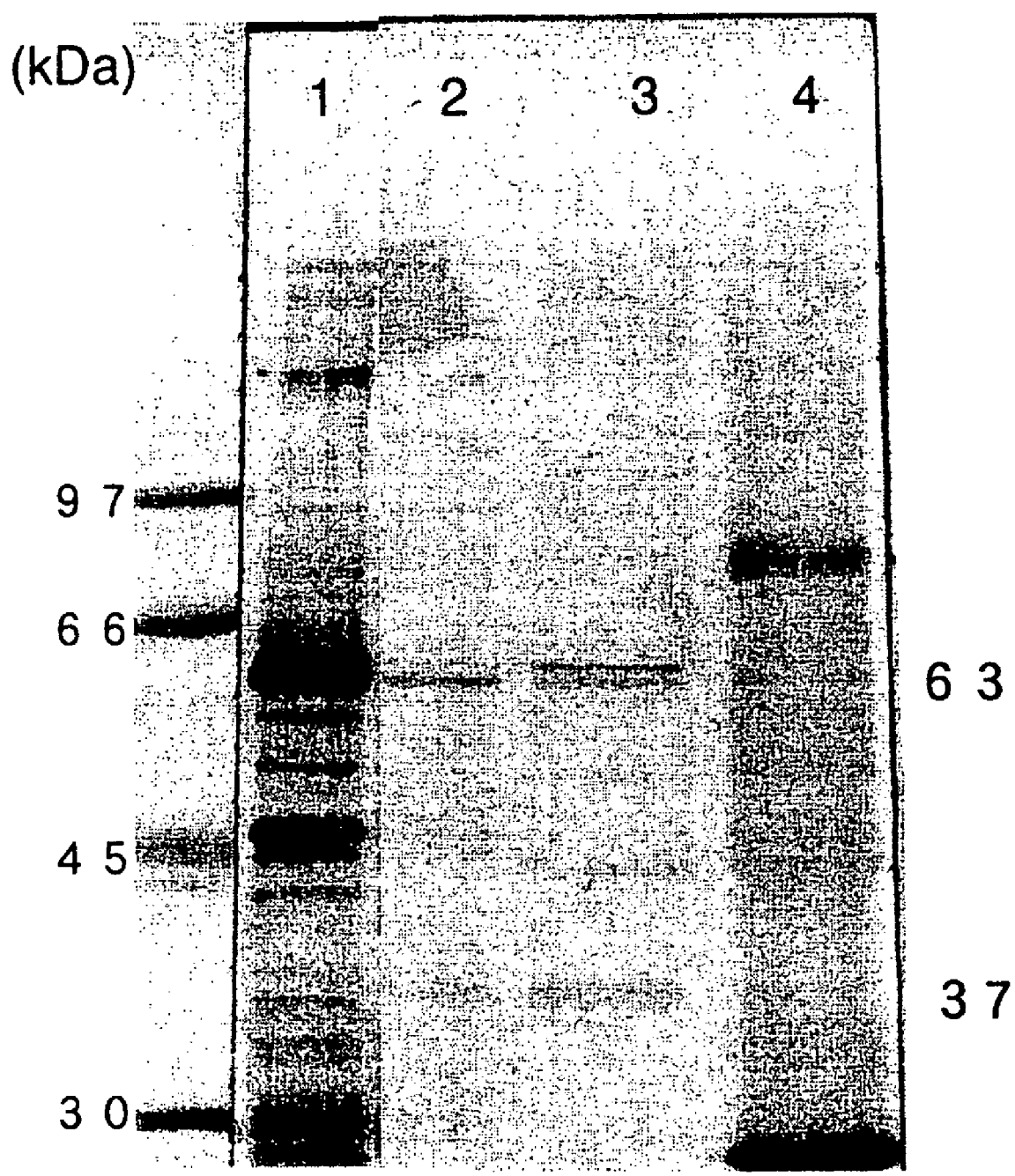
FIG. 3 shows the result of electrophoresis by immunoblotting using a anti-recombinant galectin fusion protein mouse serum.

The result is shown in lanes 2 and 3 in FIG. 3. Lanes 1 and 4 are the results obtained in Example 9.

In FIG. 3, lane 2 is the result of the hemolymph from Ornithodoros moubata 4th instar nymphs after 6 days from engorgement, and lane 3 is the result of the fat body lysate. The numbers "63" and "37" at the side of lane 4 mean the molecular weight (63 kDa) of the recombinant galectin fusion protein and the molecular weight (37 kDa) of the wild type galectin protein, respectively.

As shown in lanes 2 and 3 in FIG. 3, two specific bands of 37 kDa and 43 kDa were detected in the hemolymph from Ornithodoros moubata 4th instar nymphs after 6 days from engorgement and the fat body lysate. The 37 kDa band agreed with the theoretical value (36.6 kDa) of the galectin protein. In this connection, the reason why the 43 kDa band was detected but the 37 kDa band was not detected in Example 6 seems to be due to a small amount of sample used in electrophoresis.

Example 9

Confirmation of Reactivity of Anti-Recombinant Galectin Fusion Protein Mouse Serum with Respect to Recombinant Galectin Fusion Protein In this Example, the reactivity of the anti-recombinant galectin fusion protein mouse serum obtained in Example 5 with respect to the recombinant galectin fusion protein was examined by immunoblotting. As samples, the purified recombinant galectin fusion protein derived from *Escherichia coli* transformed with plasmid pGEMEX-4T-3/n4E12-2 and expressing the recombinant galectin fusion protein (see Example 5), and the insoluble fraction (before purification) derived from *Escherichia coli* transformed with vector pGEMEX-4T-3 and expressing the GST protein were used.

The result is shown in lanes 1 and 4 in FIG. 3.

In FIG. 3, lane 1 is the result of the purified recombinant galectin fusion protein, and lane 4 is the result of the (insoluble) GST protein before purification.

As shown in lane 1 in FIG. 3, it was confirmed that the recombinant galectin fusion protein (approximately 63 kDa) reacted with the anti-recombinant galectin fusion protein mouse serum. It was shown from the result that the recombinant galectin fusion protein is one of candidates for a tick vaccine. In this connection, the normal mouse serum did not react with the recombinant galectin fusion protein.

Example 10

Confirmation of Antigenicity of Recombinant Galectin Fusion Protein Against Mouse In this Example, whether or not the recombinant galectin fusion protein prepared in Example 5 can induce an antibody production in a mouse was examined.

From 11 mice immunized with the recombinant galectin fusion protein in Example 5, 11 mouse antisera were obtained. Each mouse antiserum was reacted with a membrane onto which the purified recombinant galectin fusion protein had been previously transferred, and then an antibody which bound to the antigen was detected by a western blotting method. In this connection, two mouse antisera prepared from two mice immunized with an adjuvant were used as a control.

As a result, an antibody against the recombinant galectin fusion protein was detected in all antisera derived from mice immunized with the recombinant galectin fusion protein, whereas no antibody was detected in the control mouse antisera.

From the result, it was confirmed that production of an antibody against the recombinant galectin fusion protein was induced by immunizing the fusion protein to a mouse, and that the recombinant galectin fusion protein is useful as an anti-tick vaccine.

Example 11

Confirmation of Agglutinin Activity of Recombinant Galectin Fusion Protein to Mouse Erythrocytes In this Example, the agglutination of the recombinant galectin fusion protein to mouse erythrocytes.

More particularly, after mouse erythrocytes were washed with PBS, the purified recombinant galectin fusion protein was diluted and added to the erythrocytes, to determine the effective concentration thereof. On the basis of the determined effective concentration, lactose, which is an inhibitor of galectin, was added so that the final concentration became 10 mmol/L. Further, using the anti-galectin mouse serum prepared in Example 5, an effect of the serum to suppress agglutination by galectin was examined.

The result is shown in FIG. 4. In FIG. 4, wells 1 to 4 are the results when 5 μg, 0.25 μg, 0.025 μg, and 0.0025 μg of the recombinant galectin fusion protein were added, respectively, well 5 is the result obtained when 0.25 μg of the recombinant galectin fusion protein and 10 mmol/L lactose were added, and well 6 is the result obtained when 0.25 μg of the recombinant galectin fusion protein and 10 μL of the anti-galectin mouse serum prepared in Example 5 were added.

As shown in FIG. 4, the recombinant galectin fusion protein agglutinated mouse erythrocytes dose-dependently. Further, the reaction was inhibited by the anti-recombinant galectin fusion protein mouse serum prepared in Example 5 or 10 mmol/L lactose.

It was confirmed from the results that the recombinant galectin fusion protein exhibits a lectin activity.

Example 12

Confirmation of Galactose-Binding Activity in Recombinant Galectin Fusion Protein In this Example, a galactose-binding activity in the recombinant galectin fusion protein was examined by a batch method using lactosyl Sepharose.

More particularly, the purified recombinant galectin fusion protein and lactosyl Sepharose were mixed in a 1.5 mL-microtube, and centrifuged at 5000 rpm. The resulting pellet was washed with PBS-T three times, and eluted with 100 mmol/L lactose.

Figure 5:
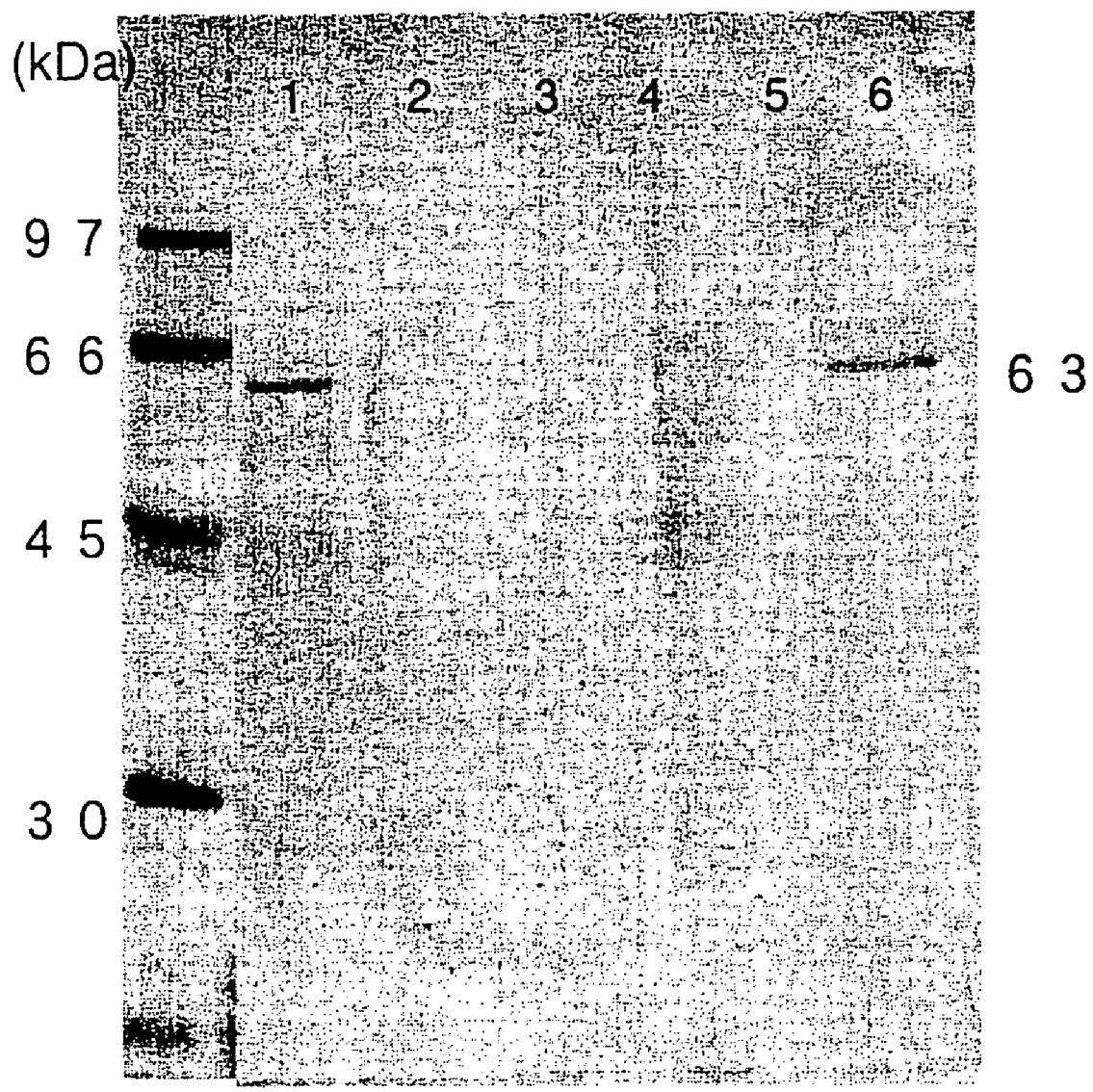
FIG. 5 shows the result of electrophoresis in a galactose-binding test for the recombinant galectin fusion protein.

The result is shown in FIG. 5. In FIG. 5, lane 1 is the result obtained when the recombinant galectin fusion protein before mixing with lactosyl Sepharose (hereinafter referred to as a preapplied sample) was electrophoresed, lane 2 is the result obtained when the supernatant obtained by centrifuging the suspended mixture of the recombinant galectin fusion protein and lactosyl Sepharose was electrophoresed, lanes 3 to 5 are the results when the first to third wash liquids were electrophoresed, respectively, and lane 6 is the result obtained when the supernatant after elution with lactose. The number "63" at the side of lane 6 means the molecular weight (63 kDa) of the recombinant galectin fusion protein.

As shown in FIG. 5, galectin was eluted with lactose (lane 6), and the amount of galectin was almost equal to that of the recombinant galectin fusion protein contained in the preapplied sample (lane 1). Further, the recombinant galectin fusion protein exhibited a property of binding to lactosyl Sepharose, and was eluted with 100 mmol/L lactose.

It was shown from the results that the recombinant galectin fusion protein exhibits a galactose-binding activity.

INDUSTRIAL APPLICABILITY

According to the polypeptide, polynucleotide, vector, transformant, and antibody of the present invention, the medicament of the present invention, particularly a tick vaccine, can be provided.

Further, according to the medicament of the present invention, particularly a tick vaccine, it is possible, for example, to exterminate ticks, or to treat or prevent tick-borne infections such as rickettsiosis, filariasis, Q fever, African recurrent fever, or viral encephalitis.

Although the present invention has been described with reference to specific embodiments, various changes and modifications obvious to those skilled in the art are possible without departing from the scope of the appended claims.

The invention claimed is:

1. A substantially pure polypeptide comprising the amino acid sequence of SEQ ID NO: 2 or a polypeptide having 90% or more identity with the amino acid sequence of SEQ ID NO: 2 and having galectin activity.

2. An isolated polynucleotide encoding the polypeptide according to claim 1.

3. An expression vector comprising the polynucleotide according to claim 2.

4. A host cell comprising the expression vector according to claim 3.

5. A method for producing a polypeptide comprising the amino acid sequence of SEQ ID NO: 2 or a polypeptide having 90% or more identity with the amino acid sequence of SEQ ID NO: 2 and having galectin activity, comprising culturing the host cell according to claim 4 under conditions promoting expression of the polypeptide, and recovering the polypeptide from the cell culture.

6. A pharmaceutical composition comprising the polypeptide according to claim 1, and a pharmaceutically or veterinary acceptable carrier or diluent.

7. A method for determining whether a test compound is a suppressor of galectin activity, said method comprising:
(a) determining the galectin activity of the polypeptide of claim 1 in the presence of a test compound, and
(b) comparing the galectin activity determined in (a) with the galectin activity determined for the polypeptide of claim 1 in the absence of the test compound, wherein when said galectin activity of the polypeptide of claim 1 is lower in the presence of said test compound than in the absence of said test compound, said test compound is determined to be a suppressor of galectin activity.

8. A method for determining whether a test compound is a promoter of galectin activity, said method comprising:
(a) determining the galectin activity of the polypeptide of claim 1 in the presence of a test compound, and
(b) comparing the galectin activity determined in (a) with the galectin activity determined for the polypeptide of claim 1 in the absence of the test compound, wherein when said galectin activity of the polypeptide of claim 1 is higher in the presence of said test compound than in the absence of said test compound, said test compound is determined to be a promoter of galectin activity.

9. A substantially pure polypeptide comprising the amino acid sequence of SEQ ID NO:2.

10. A substantially pure polypeptide consisting of the amino acid sequence of SEQ ID NO:2.

* * * * *